(12) United States Patent
Brow

(10) Patent No.: US 10,039,648 B2
(45) Date of Patent: Aug. 7, 2018

(54) INTERVERTEBRAL IMPLANT DEVICE

(71) Applicant: CHOICE SPINE, LP, Knoxville, TN (US)

(72) Inventor: Michael J. Brow, Knoxville, TN (US)

(73) Assignee: Choice Spine, LP, Knoxville, TN (US)

( * ) Notice: Subject to any disclaimer, the term of this patent is extended or adjusted under 35 U.S.C. 154(b) by 564 days.

(21) Appl. No.: 14/705,206

(22) Filed: May 6, 2015

(65) Prior Publication Data
US 2016/0324652 A1    Nov. 10, 2016

(51) Int. Cl.
| | |
|---|---|
| *A61F 2/44* | (2006.01) |
| *A61B 17/80* | (2006.01) |
| *A61F 2/30* | (2006.01) |
| *A61F 2/46* | (2006.01) |
| *A61F 2/28* | (2006.01) |

(52) U.S. Cl.
CPC .......... *A61F 2/447* (2013.01); *A61B 17/8033* (2013.01); *A61B 17/8052* (2013.01); *A61F 2/4611* (2013.01); *A61F 2002/2835* (2013.01); *A61F 2002/305* (2013.01); *A61F 2002/30014* (2013.01); *A61F 2002/3038* (2013.01); *A61F 2002/30266* (2013.01); *A61F 2002/30383* (2013.01); *A61F 2002/30578* (2013.01); *A61F 2002/30787* (2013.01)

(58) Field of Classification Search
None
See application file for complete search history.

(56) References Cited

U.S. PATENT DOCUMENTS

| | | |
|---|---|---|
| 5,397,364 A | 3/1995 | Kozak et al. |
| 6,206,922 B1 | 3/2001 | Zbeblick et al. |
| | (Continued) | |

FOREIGN PATENT DOCUMENTS

| | | |
|---|---|---|
| CN | 104546095 A | 4/2015 |
| EP | 1847240 A1 | 10/2007 |
| | (Continued) | |

OTHER PUBLICATIONS

International Searching Authority, International Search Report and Written Opinion (10 pages) dated May 13, 2016, PCT/US16/20413.

(Continued)

*Primary Examiner* — David Isabella
*Assistant Examiner* — Christine Nelson
(74) *Attorney, Agent, or Firm* — Luedeka Neely Group, PC

(57) ABSTRACT

An intervertebral implant system installable between a pair of vertebrae. The implant includes a spacer that fits between the pair of vertebrae with a screw aperture for passage of a first screw and angled to orient the first screw into a first vertebrae at an angle relative to the rear sidewall of the spacer so that the first screw will enter an endplate of the first vertebrae. A plate is installable onto the rear sidewall of the polymeric spacer. The plate includes an angled screw aperture that is aligned with the screw aperture of the spacer when the plate is installed on the spacer. An elevated screw support extends upwardly or downwardly from the plate so as to extend opposite the direction of the angled screw aperture. The elevated screw support locates a second screw to enter a second vertebrae through an anterior surface of the second vertebrae.

7 Claims, 15 Drawing Sheets

(56) References Cited

U.S. PATENT DOCUMENTS

| | | |
|---|---|---|
| 6,258,089 B1 | 7/2001 | Campbell et al. |
| 6,558,423 B1 | 5/2003 | Michelson |
| 6,626,907 B2 | 9/2003 | Campbell et al. |
| 6,972,019 B2 | 12/2005 | Michelson |
| 6,984,234 B2 | 1/2006 | Bray |
| 7,033,394 B2 | 4/2006 | Michelson |
| 7,875,076 B2 | 1/2011 | Mathieu et al. |
| 7,972,363 B2 | 7/2011 | Moskowitz et al. |
| 8,328,872 B2 | 12/2012 | Duffield et al. |
| 8,641,768 B2 | 2/2014 | Duffield et al. |
| 2007/0250167 A1* | 10/2007 | Bray ............... A61F 2/4455 623/17.11 |
| 2009/0105830 A1 | 4/2009 | Jones et al. |
| 2010/0145459 A1 | 6/2010 | McDonough et al. |
| 2010/0217393 A1* | 8/2010 | Theofilos ......... A61F 2/4455 623/17.11 |
| 2012/0277872 A1 | 11/2012 | Kana et al. |
| 2012/0330419 A1 | 12/2012 | Moskowitz et al. |
| 2014/0277456 A1* | 9/2014 | Kirschman ....... A61F 2/4455 623/17.11 |

FOREIGN PATENT DOCUMENTS

| | | |
|---|---|---|
| WO | 2010054208 A1 | 5/2010 |
| WO | 2010096773 A1 | 8/2010 |

OTHER PUBLICATIONS

Yu Chen, Xinwei Wang, Xuhua Lu, Lili Yang, Haisong Yang, Wen Yuan, Deyu Chen Comparison of titanium and polyetheretherketone (PEEK) cages in the surgical treatment of multilevel cervical spondylotic myelopathy; a prospective, randomized, control study with over 7 year follow up published on line Apr. 9, 2013 Springer-Verlag Berlin Heidelberg (8 pages).

* cited by examiner

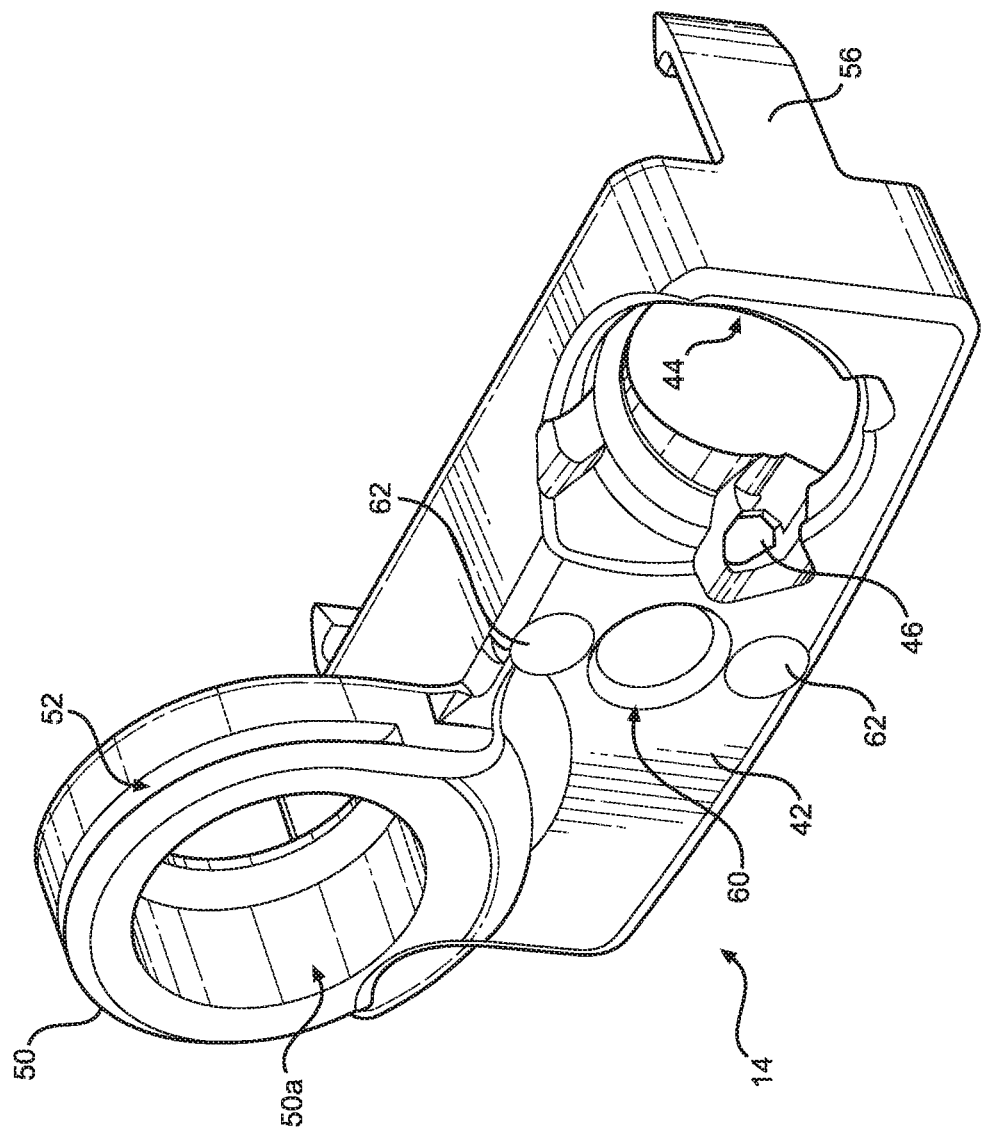

INTERVERTEBRAL IMPLANT DEVICE

FIELD

The present disclosure relates to an intervertebral implant. More particularly, the disclosure relates to an intervertebral implant that facilitates installation of screws as compared to conventional zero profile implants, while minimizing structure that extends outside the space between the vertebrae.

BACKGROUND

Improvement is desired in the construction of intervertebral implants for fusing or otherwise securing and positioning adjacent vertebrae relative to one another.

Conventional zero profile implants are difficult to access for placing screws, especially when the implant is located near the chest or chin of a patient.

The present disclosure advantageously provides a reduced profile implant configured for improved access for installation. In this regard, the implant is configured to be installed between a pair of vertebrae using a single pair of screws, with one of the screws being installable into enter an endplate of a vertebrae, and the other screw being installable into an anterior surface of an adjacent vertebrae.

SUMMARY

The disclosure relates to an intervertebral implant installable between a pair of vertebrae.

In one aspect, the implant includes a spacer having top and bottom surfaces located to fit between the pair of vertebrae. The spacer includes a rear sidewall having a screw aperture for passage of a first screw and angled to orient the first screw into a first vertebrae of the pair of vertebrae at an angle relative to the rear sidewall of the spacer so that the first screw will enter an endplate of the first vertebrae.

The implant also includes a plate installable onto the rear sidewall of the polymeric spacer. The plate includes an interior side for abutting the rear sidewall of the spacer and an opposite outer side, and an angled screw aperture that extends in an angled direction between the interior side and the outer side of the plate and is aligned with the screw aperture of the spacer when the plate is installed on the spacer. The first screw is received by the angled screw aperture and then passes through the screw aperture of the spacer to enter an endplate of the first vertebrae.

An elevated screw support extends upwardly or downwardly from the plate so as to extend opposite the direction of the angled screw aperture. The elevated screw support includes an aperture for receiving a second screw and oriented substantially normal to the outer side of the plate and substantially parallel to the top and bottom surfaces of the spacer to locate the second screw to enter a second vertebrae of the pair of vertebrae through an anterior surface of the second vertebrae.

The disclosure advantageously provides an implant structure that facilitates installation of screws as compared to conventional zero profile implants, while minimizing structure that extends outside the space between the vertebrae.

BRIEF DESCRIPTION OF THE DRAWINGS

Further advantages of the disclosure are apparent by reference to the detailed description when considered in conjunction with the figures, which are not to scale so as to more clearly show the details, wherein like reference numbers indicate like elements throughout the several views, and wherein:

FIGS. 11-14 show a plate component of the implant of FIGS. 1 and 2.

DETAILED DESCRIPTION

Figure 1:
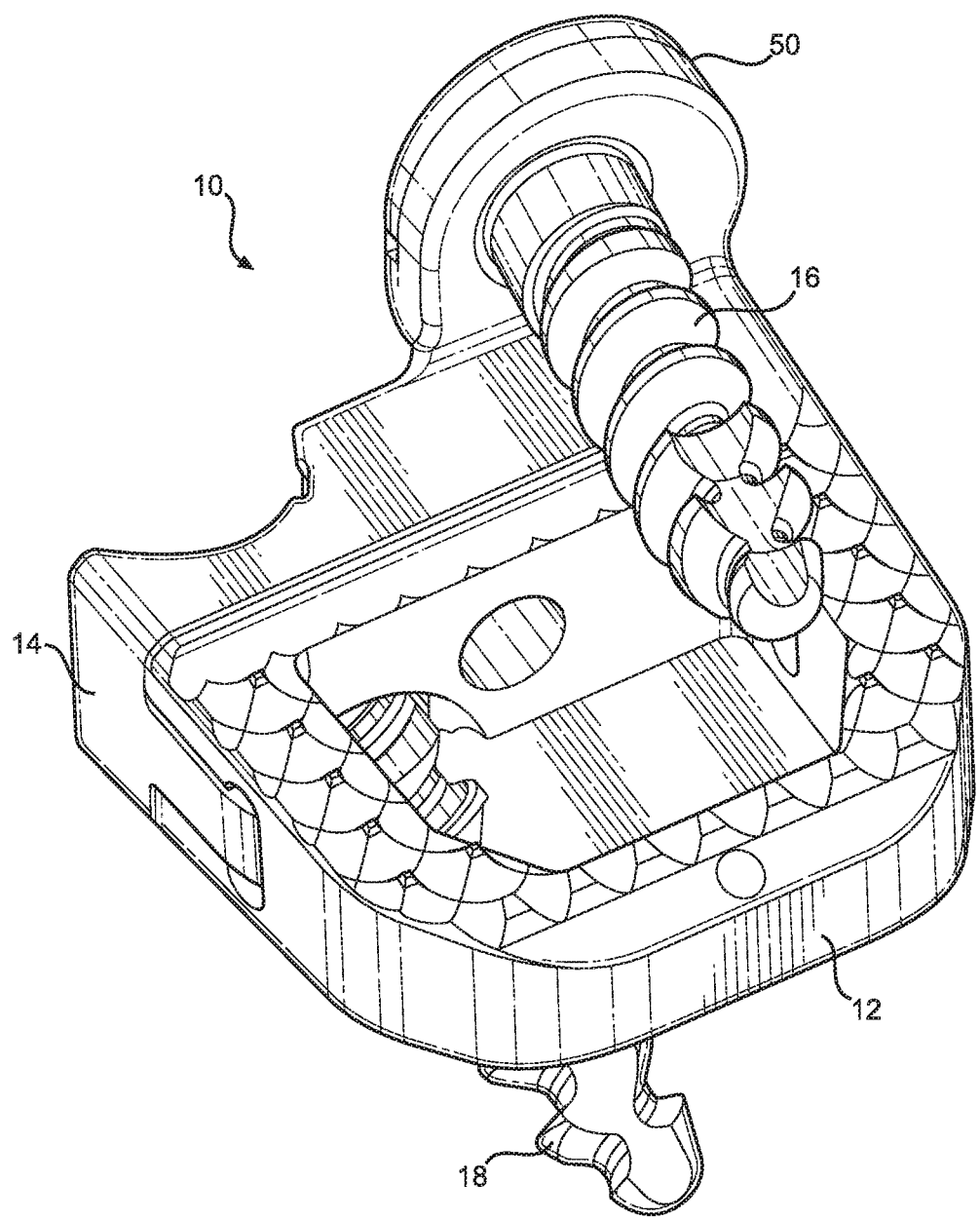
FIGS. 1 and 2 are assembled perspective views of an interverterbral implant according to the disclosure.
Figure 2:
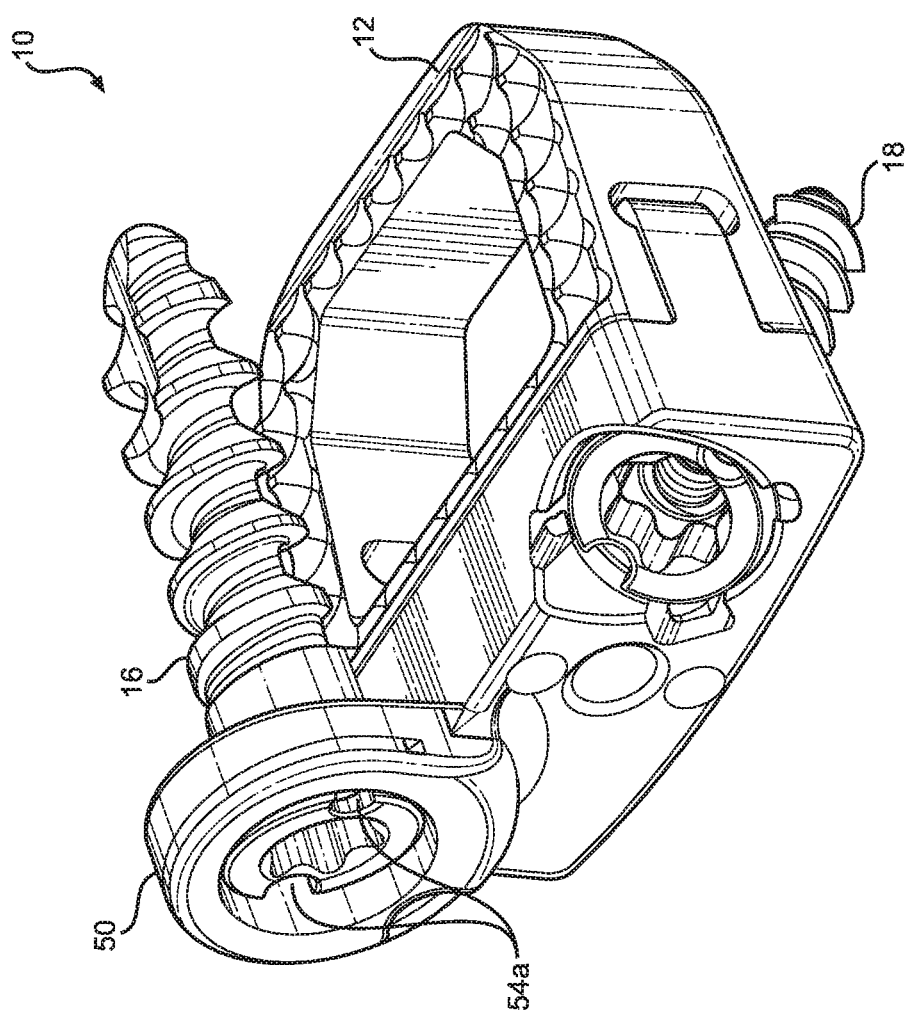

With reference to the drawings, there is shown an intervertebral implant 10 according to the disclosure having a spacer 12, a plate 14, and screws 16 and 18. The spacer 12 and plate 14 are configured to be snap fit to one another.

The implant 10 is configured to be positioned between adjacent vertebrae to space and otherwise position the vertebrae relative to one another and to limit relative movement of the vertebrae and to one another. The screw 16 is installed into one of the vertebrae and the screw 18 is installed in the adjacent vertebrae.

The structure associated with the screw 16 provides a low-profile feature, in that only minimal structure extends slightly outside of the space between the vertebrae. The structure associated with the screw 18 provides a zero profile feature in that no structure extends outside the space between the vertebrae.

As will be observed, the implant 10 is configured so that the screw 16 is oriented to be inserted straight in, or at a substantially low or zero angle orientation, so that the screw 16 will enter through an anterior surface of the vertebrae into which it is installed. The screw 18 is oriented to be at an angle of from about 30 to about 50 degrees, so that the screw 18 will enter an endplate of the vertebrae into which it is installed. The angled orientation of the screw 18 is advantageous to avoid having structure of the implant 110 that extends outside of the vertebrae. However, the angled orientation of the screw 18 provides difficulties in installation of the implant.

The screw 16 is installed straight in or horizontally, which avoids many installation difficulties. Thus, the combination of having an implant configured to have one screw installed straight in and another installed at an angled orientation advantageously provides an implant that is relatively low profile, while avoiding difficulties with installation associated with conventional zero profile implants, especially when the implant is located proximate the chin or chest.

Figure 3:
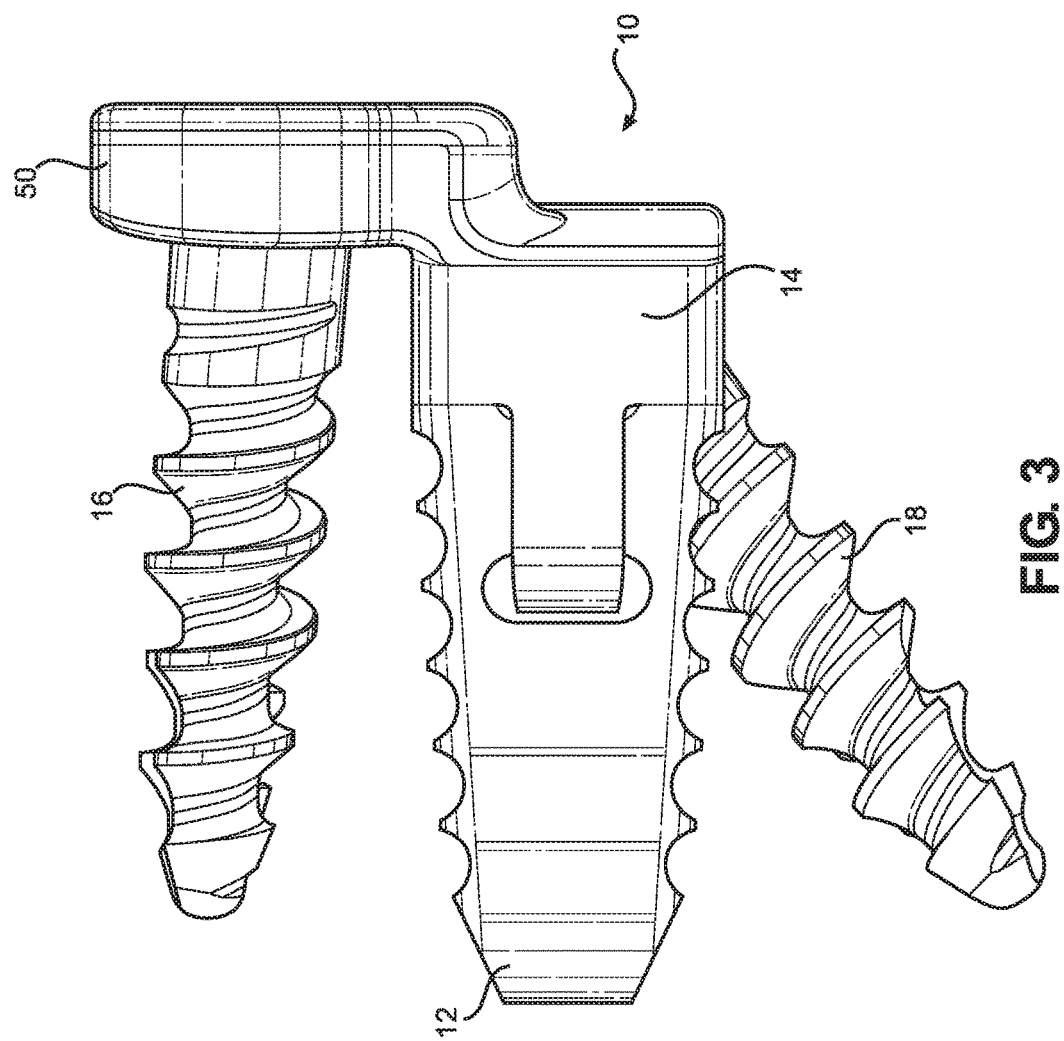
FIGS. 3 and 4 are side views of the implant of FIGS. 1 and 2.

For example, as shown in FIG. 3, the implant 10 is oriented for an installation where it would be difficult to install a screw at an upward angle. Thus, in the orientation of the implant 10 as shown in FIG. 3, the screw 16 is oriented at the upper side of the implant 10 and a surgeon will be able to install the screw 16 straight into a vertebrae. The screw 18 in this case may be easily accessed at its downward orientation.

Figure 4:
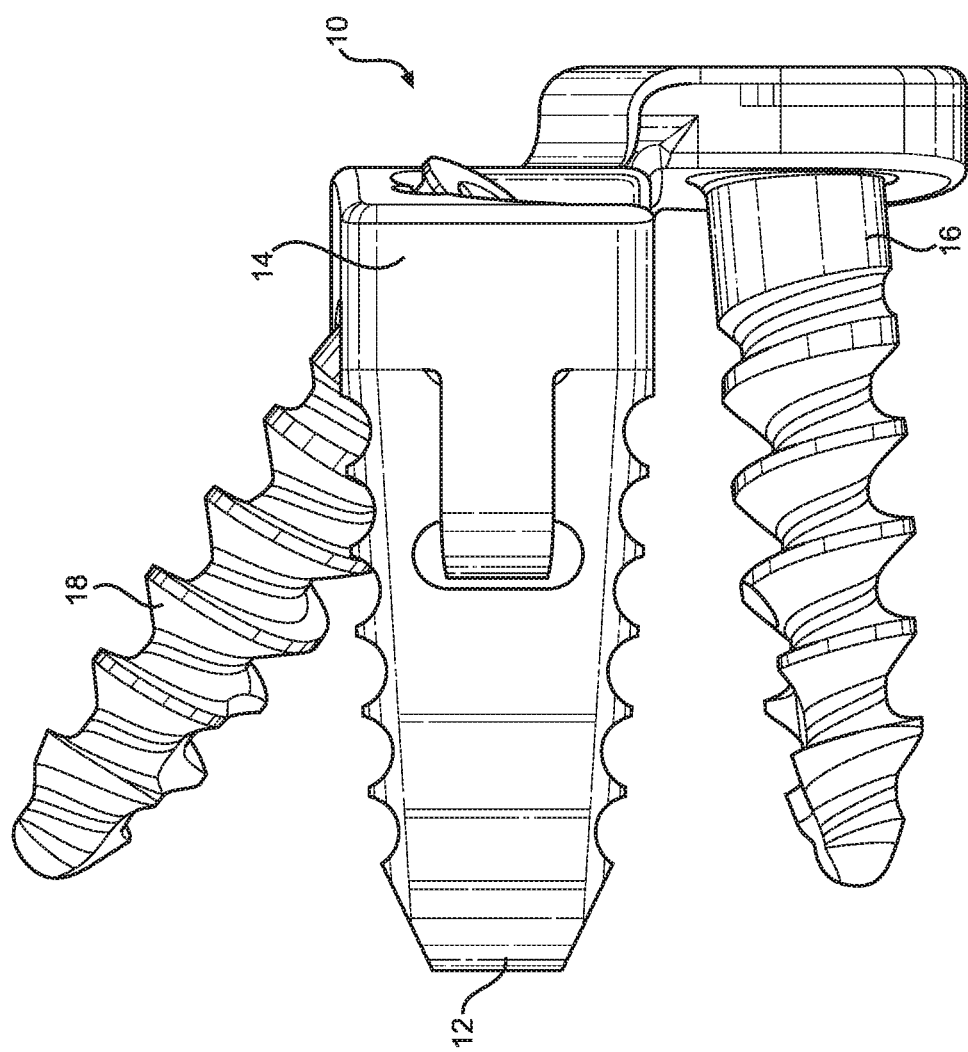
Figure 5:
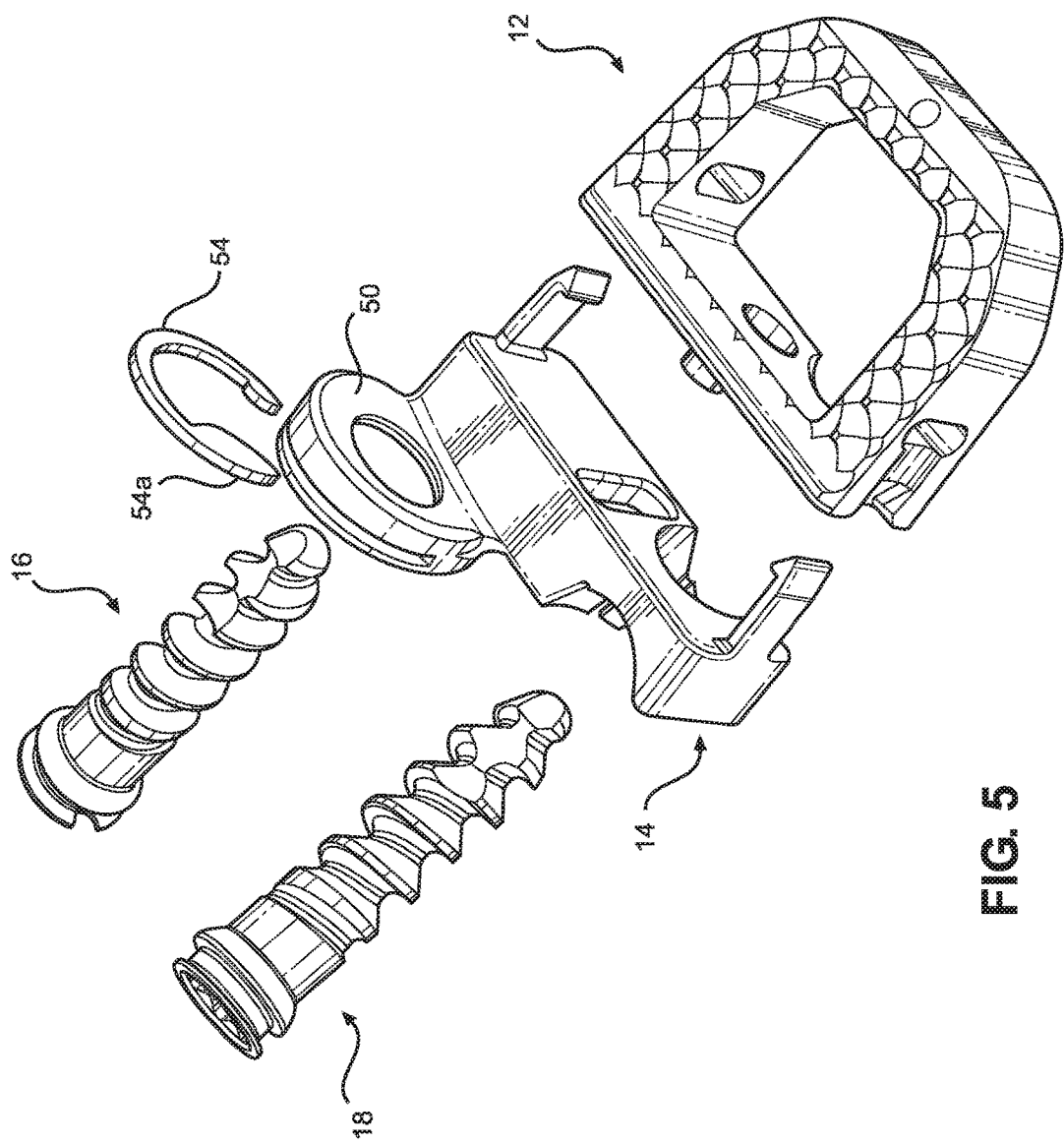
FIGS. 5 and 6 are exploded perspective views of the implant of FIGS. 1 and 2.
Figure 6:
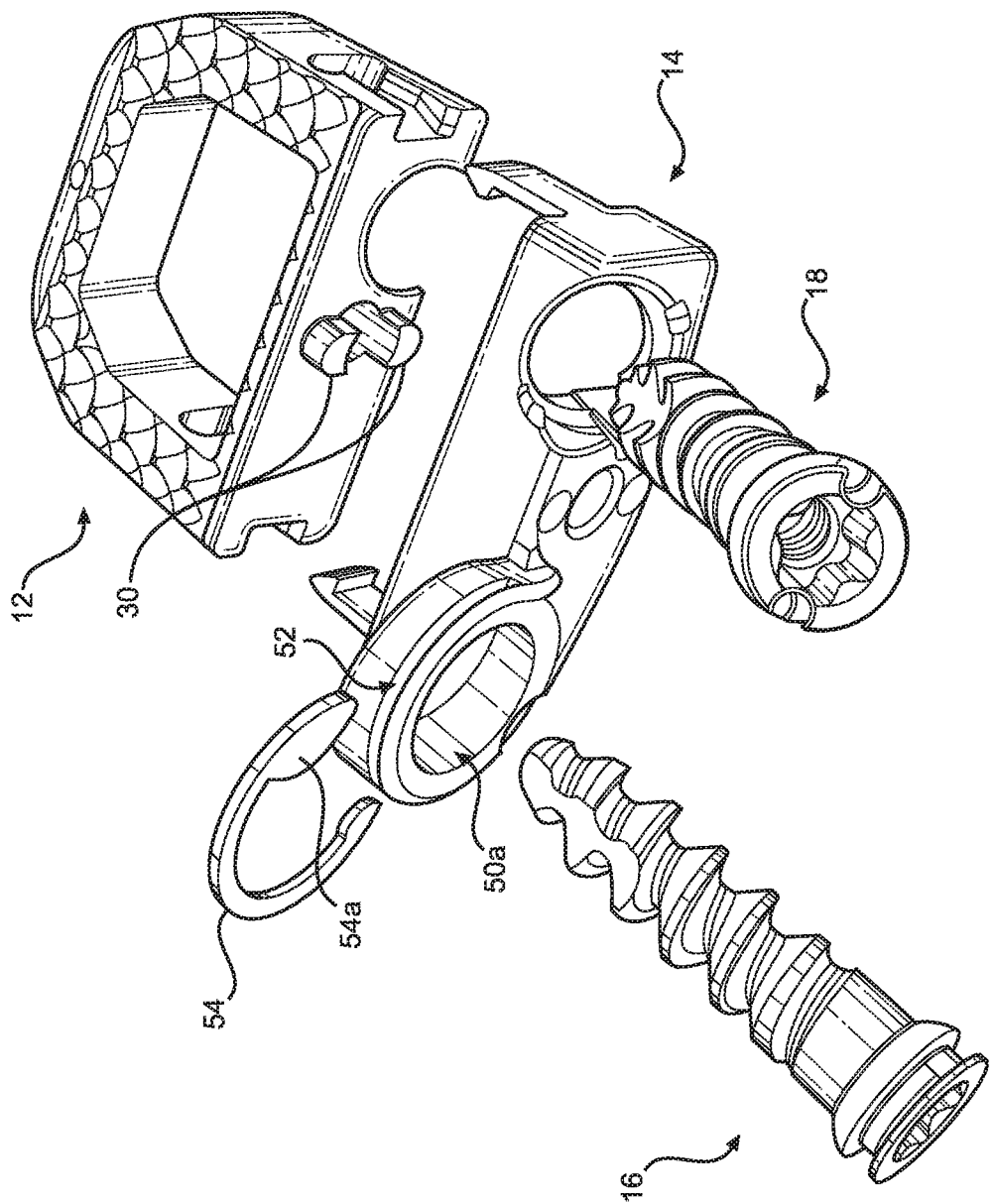

However, if the installation site is different such that a downward orientation results in a difficult installation angle, such as an installation near the chin, the implant 10 may be reversed, such as shown in FIG. 4, so that the screw 16 is oriented at the lower side of the implant 10 and a surgeon will be able to install the screw 16 straight into a vertebrae. The screw 18 may be easily accessed at its upward orientation.

Figure 8:
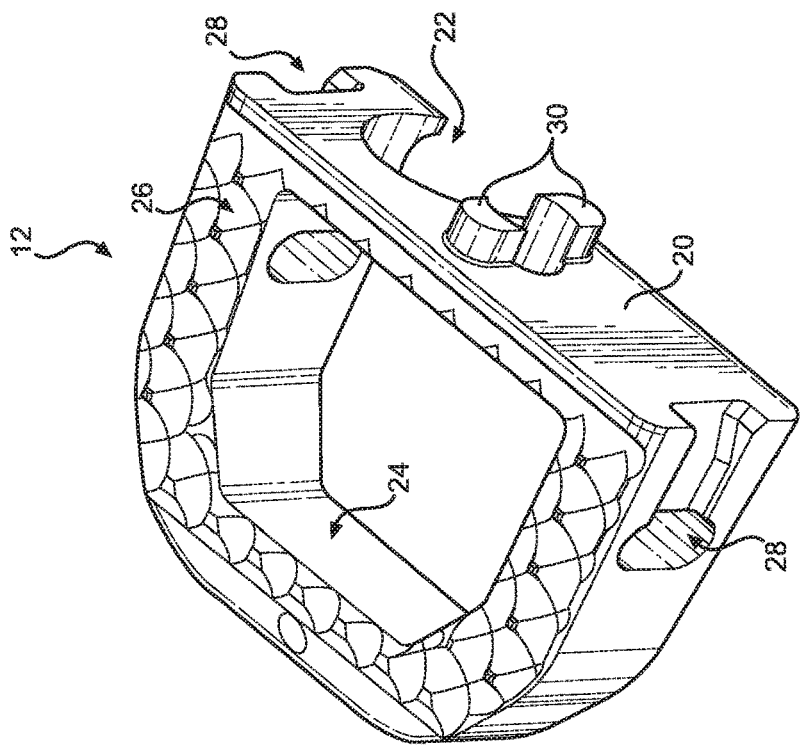
FIGS. 7-10 show a spacer component of the implant of FIGS. 1 and 2.
Figure 7:
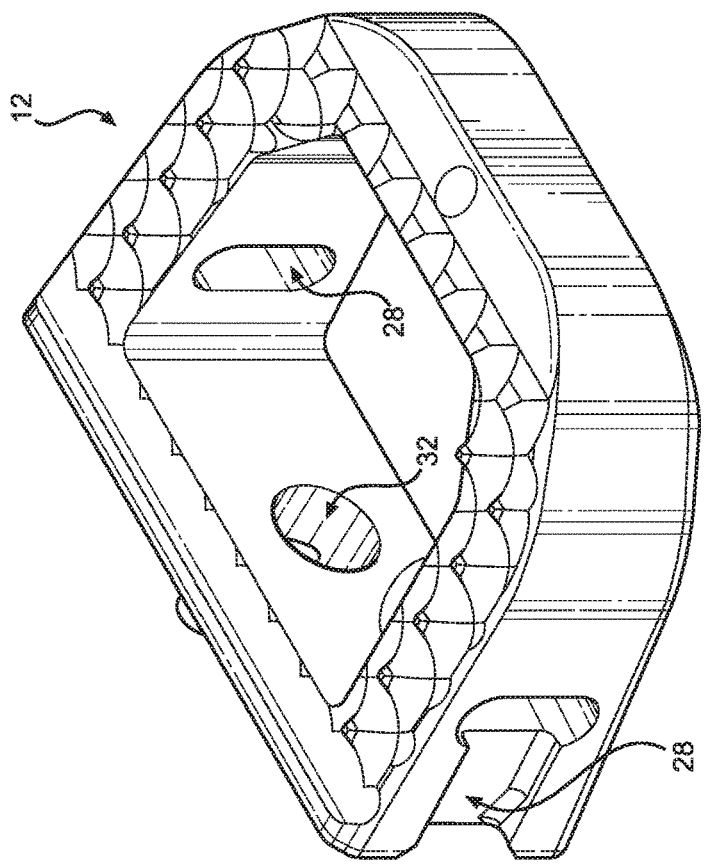
Figure 10:
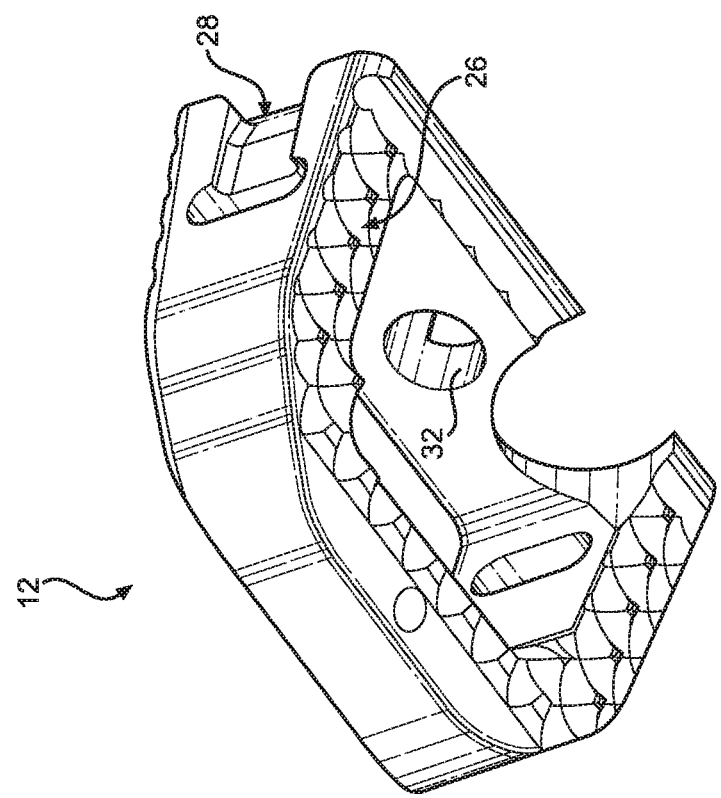
Figure 9:
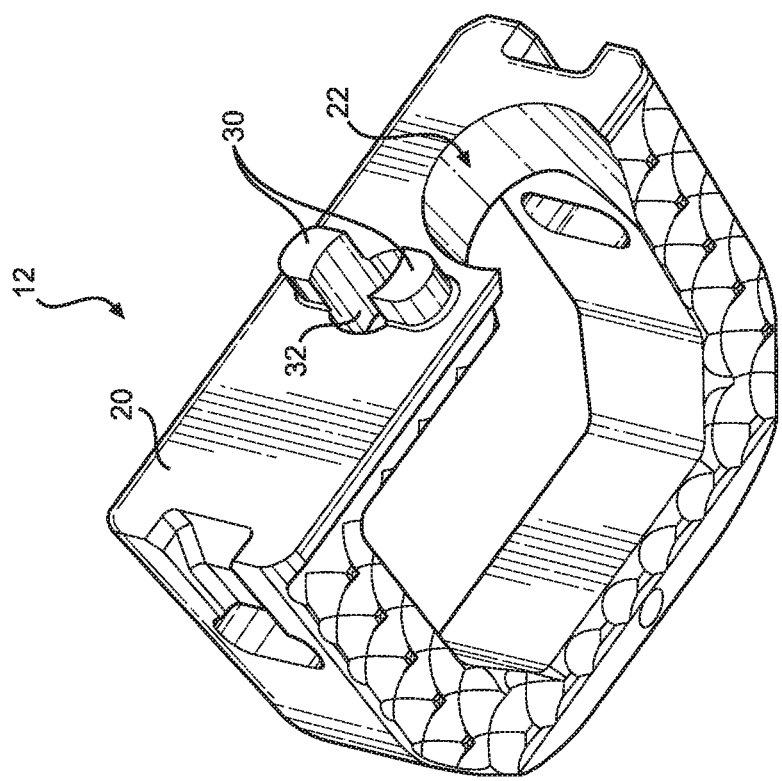
Figure 12:
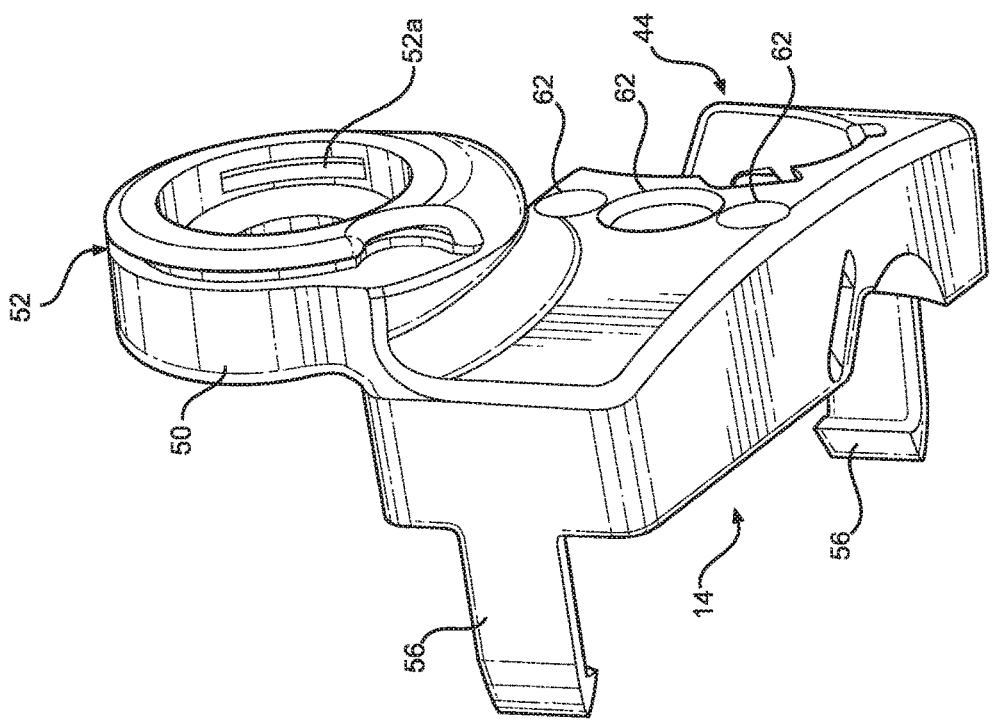
Figure 13:
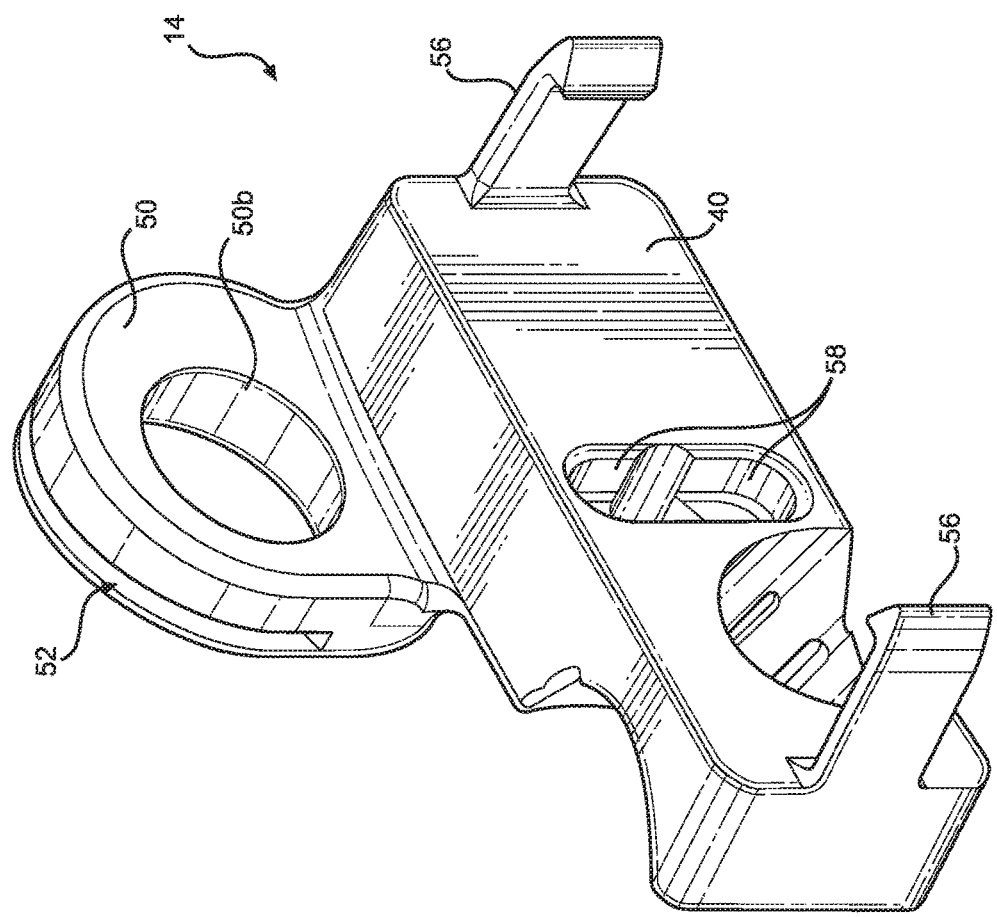
Figure 14:
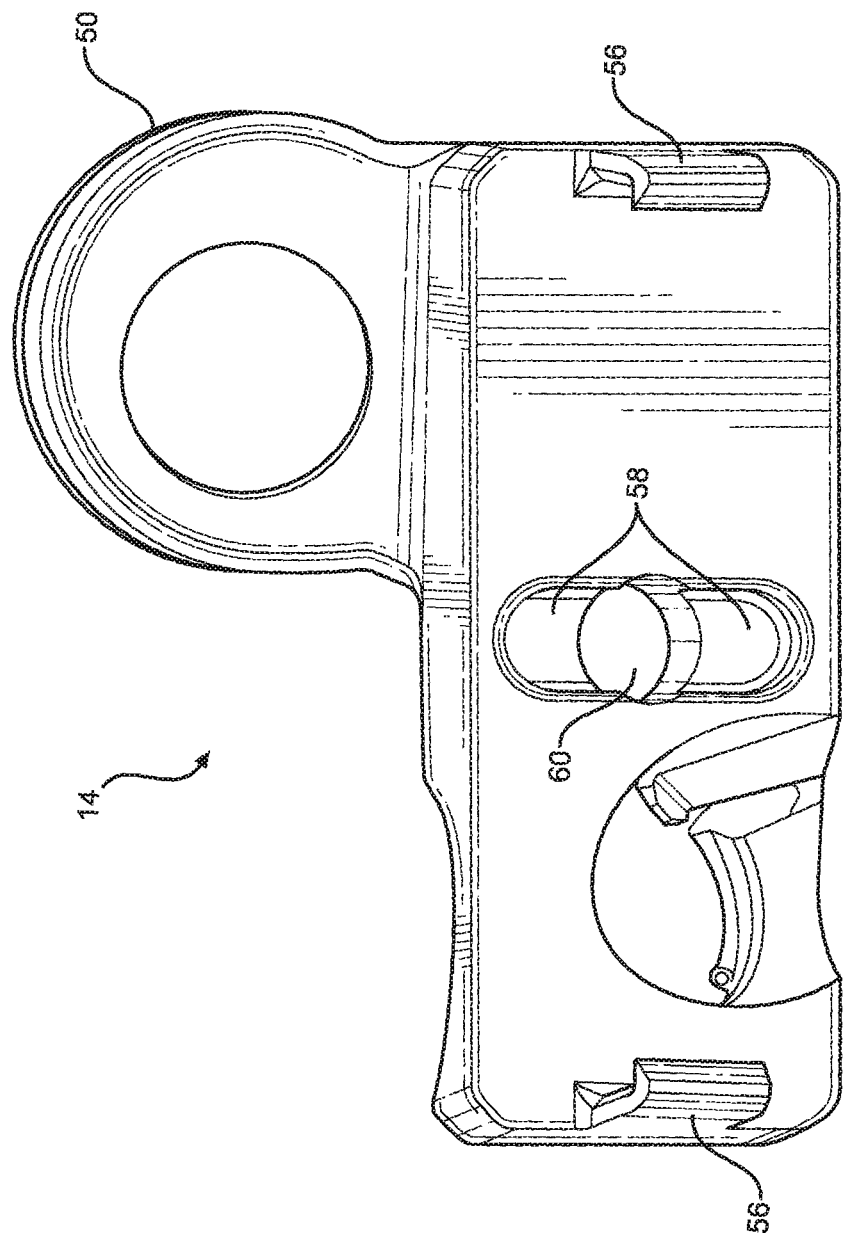

The spacer 12 is configured as a ring and is preferably made of a polyether ether ketone (peek) polymer to more closely match the elastic modulous of the vertebrae. The ring structure in conjunction with the peek material creates a platform with a desirable modulus. A rear sidewall 20 of the spacer 12 includes a single partial screw aperture 22 for passage of the screw 18 (FIG. 8). The screw aperture 22 is located adjacent a side edge, such as the right side edge of the sidewall 20 as shown. The screw aperture 22 is desirably angled to orient the screw 18 into a vertebrae at an angle relative to the sidewall 20 so that the screw 18 will enter an endplate of the vertebrae into which it is installed.

The spacer 12 also includes a central graft window 24 to promote bone growth and fusion. The spacer 12 also includes rugous top and bottom surfaces, such as having ridges 26 thereon, to inhibit movement and expulsion of the implant 10 from its installation between the vertebrae. The spacer includes recesses 28 on opposite sides of the spacer 12 to provide a snap-fit attachment of the spacer 12 and plate 14. Projections 30 are centrally located on the sidewall 20 for cooperating with the plate 14 for facilitating seating of the plate 14. An aperture 32 is centrally located on the sidewall 20 for receiving instrumentation for placement of the implant 10.

Figure 17:
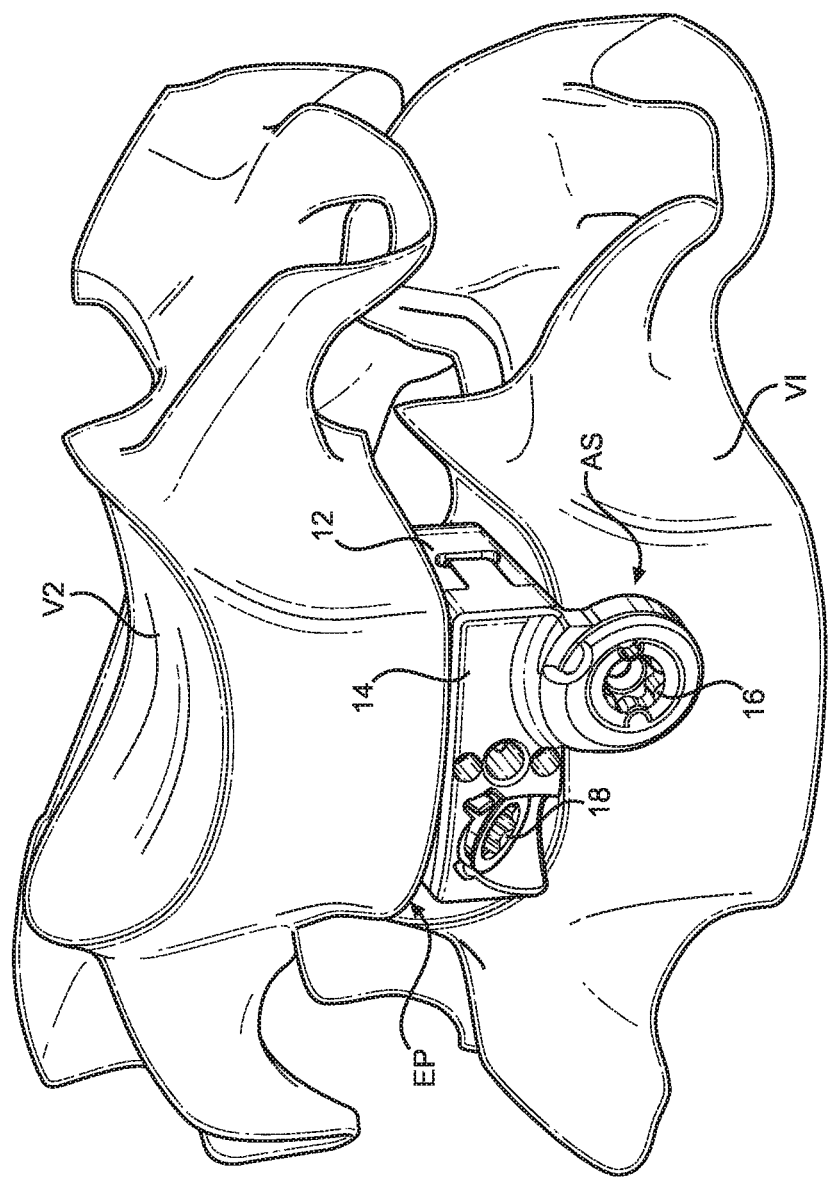
FIGS. 17 and 18 show the implant of FIGS. 1 and 2 installed onto vertebrae of a spine.
Figure 18:
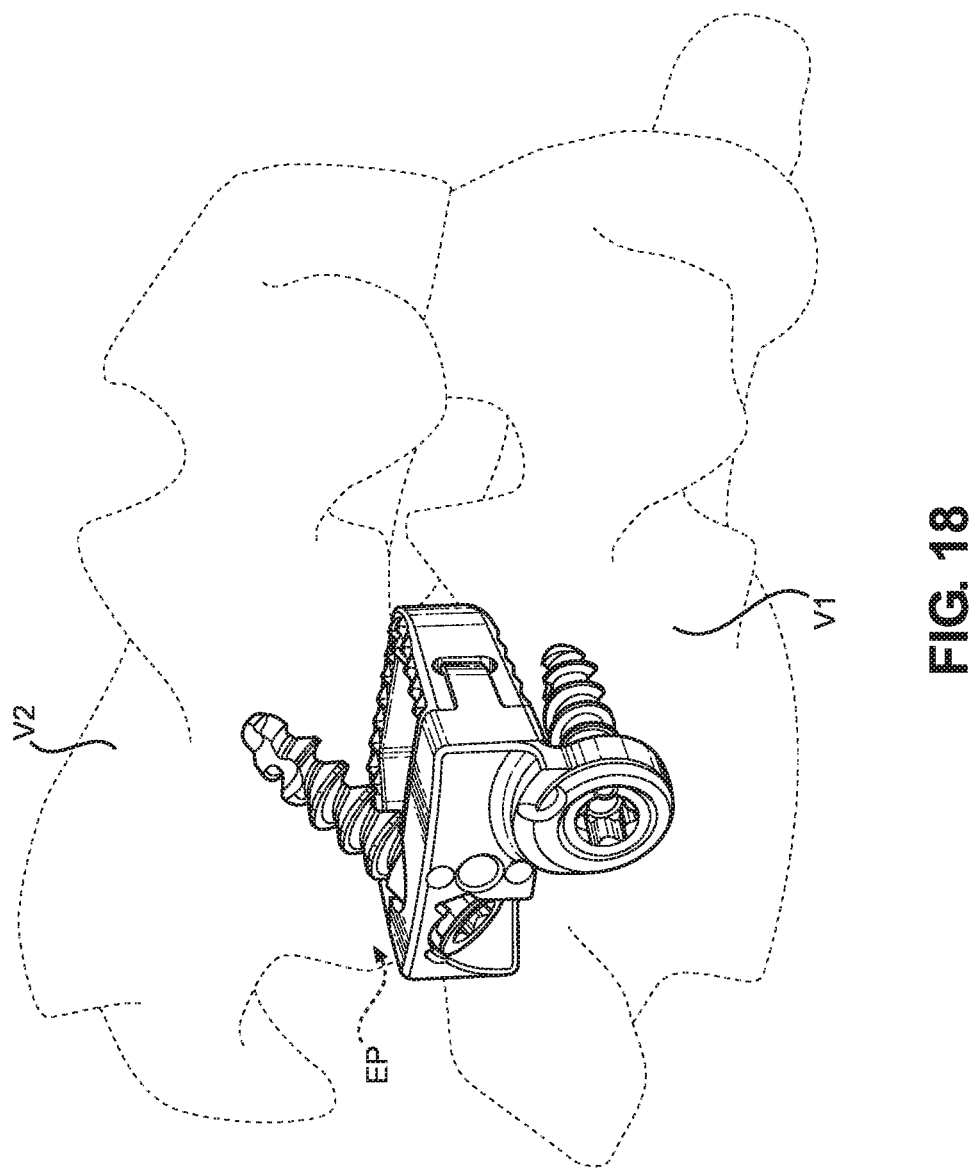

The plate 14 is preferably a rigid plate made of a titanium alloy to provide a support housing for the bearing forces of the heads of the screws 16 and 18. The plate 14 is generally rectangular and includes an interior side 40 for abutting the rear sidewall 20 of the spacer 12. An opposite outer side 42 of the plate 14 is configured to include an angled screw aperture 44 that extends between the sides 40 and 42 and aligns with the screw aperture 22 of the spacer 12. The screw aperture 44 extends at an inclination or declination depending on the orientation of the implant 10. The screw 18 is received by the screw aperture 44 and then passes through the screw aperture 22 of the spacer 12 to enter an endplate of the vertebrae into which it is installed (FIGS. 17 and 18).

The screw aperture 44 includes a machined tang 46 that deflects as the screw 18 passes to permit the screw 18 to be installed. Once the screw 18 is fully installed, the tang 46 relaxes to intrude into the screw aperture 44 to inhibit the screw 18 from backing out. In addition, the screw 18 may include slots 48 or other structure on the screw head which the tang 46 may engage to further prevent screw migration when the screw 18 is seated.

The plate 14 also includes structure to permit the screw 16 to be installed. In this regard, an elevated screw support 50 extends upwardly (or downwardly) opposite the direction of the angled aperture 44. The screw support 50 is desirably substantially flush with the outer side 42 of the plate 14 to minimize the profile of the implant 10. The screw support 50 is desirably formed as a ring and includes a central aperture 50a for receiving the screw 16.

That is, from the orientation of the plate 14 shown, the aperture 44 is angled down, and the screw support 50 extends upwardly from the surface 42 of the plate 14. If the plate 14 were reversed in orientation, the aperture 44 would be angled upwardly and the screw support 50 would extend down. However, the screw support 50 provides an aperture direction that is substantially normal to the side 42 and parallel to the top and bottom surfaces of the spacer 12. Thus, the screw support 50 locates the screw 16 to enter a vertebrae through an anterior surface of the vertebrae (FIGS. 17 and 18).

A circumferential groove 52 surrounds the screw support 50 for receiving a screw retention clip 54. The clip 54 is preferably made of nitinol and includes a lobe 54a that extend through an opening 52a in the groove 52 to block the screw head of the installed screw 16 from backing out of the aperture 50a of the screw support 50.

The plate 14 includes attachment arms 56 that extend from each side of the plate 14 and are configured to latch and seat into the corresponding recesses 28 of the spacer 12 to provide a snap-fit attachment of the spacer 12 and plate 14. The interior side 40 of the plate 14 includes detents 58 that align with and receive the projections 30 of the spacer 12. Thus, when the plate 14 is snap fit to the spacer 12, the arms 56 as well as the mating detents 58 and projections 30 help to maintain the snap fit structure as a unitary structure. An aperture 60 extends through the plate 14 and aligns with the aperture 32 of the spacer 12 for receiving instrumentation for placement of the implant. The outer side 42 of the plate 14 may include additional centrally located inserter features, such as detents 62, to engage instrumentation for placement of the implant 10.

Figure 15:
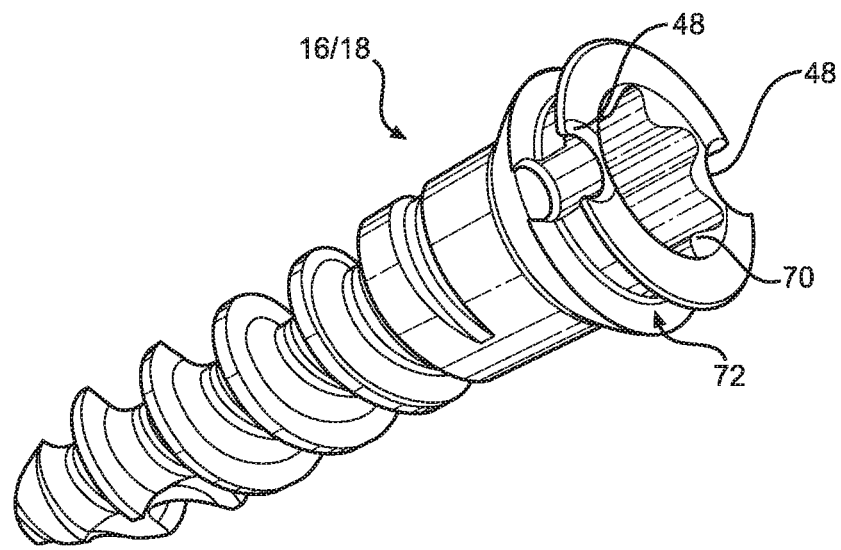
FIGS. 15-16 show a screw component of the implant of FIGS. 1 and 2.
Figure 16:
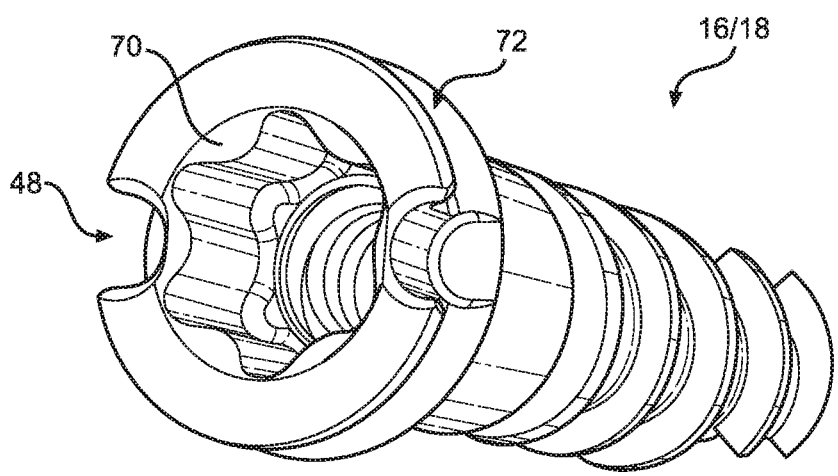

The screws 16 and 18 may be identical. With reference to FIGS. 15 and 16 the screws 16 and 18 additionally include a head 70 configured to receive a driver for installation of the screws. The screws 16/18 also include an annular groove 72 for cooperating with the anti-backout structures, such as the tang 46 and lobes 54a.

With reference to FIGS. 17 and 18, there is shown the implant 10 installed between vertebrae V1 and vertebrae V2. As will be seen, the screw 16 enters the vertebrae V1 to the right of the midline of the vertebrae V1 and through an anterior surface AS of the vertebrae V1. Accordingly, the structure of the implant 10 associated with the screw 16 provides a low-profile feature, in that the screw support 50 extends slightly outside of the space between the vertebrae.

The screw 18 enters the vertebrae V2 to the left of the midline of the vertebrae V2 and through an endplate EP of the vertebrae V2. Accordingly, the structure associated with the screw 18 provides a zero profile feature in that no structure extends outside the space between the vertebrae.

Thus, the implant 10 advantageously provides an implant structure that utilizes only a pair of screws and provides a low profile structure with one screw being installed so as to be wholly between the vertebrae. The implant structure facilitates installation of screws as compared to conventional zero profile implants, while minimizing structure that extends outside the space between the vertebrae.

The foregoing description of preferred embodiments for this disclosure has been presented for purposes of illustration and description. It is not intended to be exhaustive or to limit the disclosure to the precise form disclosed. Obvious modifications or variations are possible in light of the above teachings. The embodiments are chosen and described in an effort to provide the best illustrations of the principles of the disclosure and its practical application, and to thereby enable one of ordinary skill in the art to utilize the disclosure in various embodiments and with various modifications as are suited to the particular use contemplated.

The invention claimed is:

1. An intervertebral implant system consisting of a pair of screws installable between a pair of vertebrae to provide a space between the pair of vertebrae defined by a spacer of the intervertebral implant system, the implant system comprising:

the spacer having top and bottom surfaces locatable to fit in the space between the pair of vertebrae and having a rear sidewall having a screw aperture for passage of a first screw and angled to orient the first screw into a first vertebrae of the pair of vertebrae at an angle relative to the rear sidewall of the spacer so that the first screw will enter an endplate of the first vertebrae at an angle of about 30 to about 50 degrees relative to the top and bottom surfaces of the spacer; and a plate installable onto the rear sidewall of the spacer, the plate comprising:

an interior side for abutting the rear sidewall of the spacer and an opposite outer side, an angled screw aperture that extends in an angled direction between the interior side and the outer side of the plate and is aligned with the screw aperture of the spacer when the plate is installed on the spacer, wherein the first screw is received by the angled screw aperture and then passes through the screw aperture of the spacer to enter an endplate of the first vertebrae wherein the angled screw aperture does not extend beyond the space between the vertebrae when the implant system is installed between the pair of vertebrae, and a single elevated screw support extending upwardly or downwardly from the plate so as to extend opposite the direction of the angled screw aperture, the elevated screw support including an aperture for receiving a second screw and oriented substantially normal to the outer side of the plate and substantially parallel to the top and bottom surfaces of the spacer to locate the second screw to enter a second vertebrae of the pair of vertebrae through an anterior surface of the second vertebrae.

2. The system of claim 1, wherein the spacer is made of polymeric material and the plate is made of metal.

3. The system of claim 1, wherein the plate includes arms and the spacer includes receivers for the arms so that the plate is snap fit onto the spacer.

4. The system of claim 1, further comprising a deflectable tang located adjacent the angled screw aperture of the plate, wherein the tang deflects as the first screw passes to permit the screw to be installed, and after the screw is installed, the tang relaxes to inhibit the screw from backing out.

5. The system of claim 1, further comprising groove surrounding a portion the elevated screw support and a screw retention clip having lobes that extend through openings in the groove to block a head of the installed second screw from backing out of the aperture of the elevated screw support.

6. An intervertebral implant system installable between a pair of vertebrae to provide a space between the pair of vertebrae defined by a spacer of the intervertebral implant system, the implant system comprising:

screws that complete the installation of the implant, the screws consisting of a first screw and a second screw;

the spacer having top and bottom surfaces locatable to fit in the space between the pair of vertebrae and having a rear sidewall having a screw aperture for passage of the first screw and angled to orient the first screw into a first vertebrae of the pair of vertebrae at an angle relative to the rear sidewall of the spacer so that the first screw will enter an endplate of the first vertebrae at an angle of about 30 to about 50 degrees relative to the top and bottom surfaces of the spacer; and a plate installable onto the rear sidewall of the spacer, the plate comprising: an interior side for abutting the rear sidewall of the spacer and an opposite outer side, an angled screw aperture that extends in an angled direction between the interior side and the outer side of the plate and is aligned with the screw aperture of the spacer when the plate is installed on the spacer, wherein the angled screw aperture does not extend beyond the space between the vertebrae when the implant system is installed between the pair of vertebrae, wherein the first screw is received by the angled screw aperture and then passes through the screw aperture of the spacer to enter an endplate of the first vertebrae, and an elevated screw support extending upwardly or downwardly from the plate so as to extend opposite the direction of the angled screw aperture, the elevated screw support including an aperture for receiving the second screw and oriented substantially normal to the outer side of the plate and substantially parallel to the top and bottom surfaces of the spacer to locate the second screw to enter a second vertebrae of the pair of vertebrae through an anterior surface of the second vertebrae.

7. An intervertebral implant system consisting of a pair of screws installable between a pair of vertebrae to provide a space between the pair of vertebrae defined by a spacer of the intervertebral implant system, the implant system comprising:

the spacer having top and bottom surfaces locatable to fit in a space defined between the pair of vertebrae and having a rear sidewall having a screw aperture for passage of a first screw and angled to orient the first screw into a first vertebrae of the pair of vertebrae at an angle relative to the rear sidewall of the spacer so that the first screw will enter an endplate of the first vertebrae at an angle of about 30 to about 50 degrees relative to the top and bottom surfaces of the spacer; and a plate installable onto the rear sidewall of the spacer, the plate consisting essentially of:

an interior side for abutting the rear sidewall of the spacer and an opposite outer side, a single angled screw aperture that extends in an angled direction between the interior side and the outer side of the plate and is aligned with the screw aperture of the spacer when the plate is installed on the spacer, wherein the first screw is received by the angled screw aperture and then passes through the screw aperture of the spacer to enter an endplate of the first vertebrae wherein the angled screw aperture does not extend beyond of the space between the vertebrae when the implant system is installed between the pair of vertebrae, and a single elevated screw support extending upwardly or downwardly from the plate so as to extend opposite the direction of the angled screw aperture, the elevated screw support including an aperture for receiving a second screw and oriented substantially normal to the outer side of the plate and substantially parallel to the top and bottom surfaces of the spacer to locate the second screw to enter a second vertebrae of the pair of vertebrae through an anterior surface of the second vertebrae.

* * * * *